(12) United States Patent
Lemaitre et al.

(10) Patent No.: US 7,326,464 B2
(45) Date of Patent: Feb. 5, 2008

(54) CALCIUM PHOSPHATE MICROGRANULES

(75) Inventors: Jacques Lemaitre, Lausanne (CH); Stephane Terrazzoni, Morges (CH)

(73) Assignee: Ecole Polytechnique Fédérale de Lausanne (EPFL), Lausanne (CH)

( * ) Notice: Subject to any disclaimer, the term of this patent is extended or adjusted under 35 U.S.C. 154(b) by 208 days.

(21) Appl. No.: 10/258,549

(22) PCT Filed: Apr. 9, 2001

(86) PCT No.: PCT/CH01/00224
§ 371 (c)(1),
(2), (4) Date: Nov. 4, 2002

(87) PCT Pub. No.: WO01/81243
PCT Pub. Date: Nov. 1, 2001

(65) Prior Publication Data
US 2004/0029699 A1    Feb. 12, 2004

(30) Foreign Application Priority Data
Apr. 26, 2000    (CH) ........................ 81400

(51) Int. Cl.
*C01B 25/16*    (2006.01)
(52) U.S. Cl. ................ 428/402; 423/308; 423/311
(58) Field of Classification Search .............. None
See application file for complete search history.

(56) References Cited
U.S. PATENT DOCUMENTS

| | | | |
|---|---|---|---|
| 3,384,451 A | 5/1968 | Volz | |
| 4,781,904 A * | 11/1988 | Tagaya et al. | 423/308 |
| 5,108,956 A * | 4/1992 | Inoue et al. | 501/1 |
| 5,651,884 A * | 7/1997 | Ichitsuka et al. | 210/198.2 |
| 5,858,318 A * | 1/1999 | Luo | 423/308 |
| 6,426,114 B1 * | 7/2002 | Troczynski et al. | 427/2.27 |

OTHER PUBLICATIONS

Database WPI; Section Ch, Week 199034, Derwent Publication Ltd., London, GB; AN 257489; XP002141907; & JP 02 180709 A; Jul. 13, 1990.
Paul et al; "Development of Porous Spherical Hydroxyapatite Granules; Application Towards Protein Delivery"; J Mater Sci Mater Med; Journal of Materials Science: Materials in Medicine 1999 Kluwer Academic Publishers, Dodrecht, Netherlands, vol. 10, No. 7, 1999, pp. 383-388, XP002142926, no month.
Database WPI; Section Ch, Week 199110, Derwent Publications Ltd., London, GB; AN 1991-068944, XP002142913; & JP 03 016906 A, Jan. 24, 1991.
Database WPI, Section Ch, Week 199034, Derwent Publications Ltd., London, GB; AN 1990-257487, XP00214914; & JP 02 180707 A, Jul. 13, 1990.
Database WPI, Section Ch, Week 199120, Derwent Publication Ltd., London, GB; AN 1991-146055, XP002142915; & JP 03 083805 A, Apr. 9, 1991.

(Continued)

*Primary Examiner*—Wayne A. Langel
(74) *Attorney, Agent, or Firm*—Nixon & Vanderhye P.C.

(57) ABSTRACT

The invention concerns microgranules produced from calcium phosphate materials. The invention also concerns a method for producing said microgranules. The inventive microgranules are characterized by a very narrow particle size distribution.

9 Claims, 2 Drawing Sheets

OTHER PUBLICATIONS

Brandenberger, H.R., et al, *Biotechnol. Prog.*, 1999, 15, 366-372 "Immobilization of Highly Concentrated Cell Suspensions Using the Laminar Jet Breakup Technique.", no month.

Brandenberger, H., et al., *Journal of Biotechnology*, 63 (1998) 73-80 "A new multinozzle encapsulation/immobilization system to produce uniform beads of alginate.", no month.

* cited by examiner

CALCIUM PHOSPHATE MICROGRANULES

This application is the US national phase of international application PCT/CH01/00224 filed 9 Apr. 2001, which designated the US.

FIELD OF THE INVENTION

The present invention is related to microgranules made of calcium phosphate materials.

This invention also concerns a process for manufacturing said microgranules.

The microgranules according to the invention can be used in many applications in the biomedical field (bone filling materials, metallic implant coating by plasma-spray, carriers for bone cells culture, or carriers for drug delivery), by virtue of their biocompatibility and of their controllable characteristics (composition, average size, size distribution, porosity, surface finish). They can also be used as stationary phase in liquid chromatography.

STATE OF THE ART

Calcium phosphate compounds, particularly hydroxyapatite and β-tricalcium phosphate, are known for being used in numerous biomedical applications, by virtue of their chemical composition close to the mineral fraction of bone which makes them perfectly biocompatible. Moreover, in contrast to inert biomaterials such as alumina and zirconia, calcium phosphate materials are bioactive and osteoconductive, meaning that they stimulate exchanges with living cells and host tissues, and promote osteogenesis.

In orthopedic and maxillo-facial surgery, when it comes to augment or replace bone tissue defects of casual or pathological origin, calcium phosphate materials are often used in the form of granules approximately spherical in shape. In this form, they can be incorporated into injectable calcium phosphate cements, aqueous solutions containing polymeric cellulose derivatives (U.S. Pat. No. 5,717,006), blood (U.S. Pat. No. 5,064,436), or alternatively they can be used in the ex-vivo manufacture of preformed ceramic implants. Admixed to orthopedic cements based on PMMA, they can be used for prosthesis sealing and for bone defect filling (U.S. Pat. No. 4,842,603). Calcium phosphate granules are also used in dental surgery, jointly with biocompatible binders, for example in alveolar ridge augmentation, dental socket filling after tooth extraction, or bone tissue augmentation (U.S. Pat. No. 5,702,677, see Hench (1991) J. Am. Cer, Soc.). In these fields of application, the diameters of the calcium phosphate granules used lie in the range 2-3 millimeters. On another hand, evidence has been shown that implanted granules should preferably be spherical with a smooth surface, in order to prevent inflammatory reactions often observed in living tissues in contact with implants showint sharp edges or angular shapes. In the case of injectable calcium phosphate cements or PMMA, the preferred granule characteristics are: diameter smaller than 200-300 micrometers, narrow particle size distribution, and shape as spherical as possible in order to confer good flowability to the injected paste. It is also possible to tune the resorption rate of the implanted granules by adjusting their porosity: for a given granule composition, the larger the pore volume fraction, the faster will be its resorption in biological conditions. Likewise, in order to prevent any encapsulation phenomenon, essentially found around large implants, implanted granules should show a homogeneous pore structure, preferably interconnected, promoting diffusional and convective transport of physiological liquids and cells, particularly macrophages (U.S. Pat. No. 5,034,352 and U.S. Pat. No. 5,064,436). In contrast, excessive porosity should be avoided in granules to be used in mechanically stressed implantation sites, for such granules would be too weak and would collapse under loading.

Calcium phosphate granules are also used for coating metallic implants by plasma spraying, as carriers for in vitro culture of bone cells (U.S. Pat. No. 4,457,017) or as excipients for the controlled release of active pharmaceutical substances. Here again, the granulates should have well defined characteristics adapted to each specific application. For example, plasma-spray techniques need granules with a very narrow size distribution, in order to improve the deposition yield, and good flowability of the powder to be sprayed in order to achieve accurate and constant feed of the spraying gun. Regarding excipients for pharmaceutical substances, it is important to achieve very uniform granule characteristics: indeed, the release rate of pharmaceutically active substances from carrying granules closely depends on their shape, size, specific surface area and porosity (U.S. Pat. No. 5,066,441 and U.S. Pat. No. 5,055,307). Any dispersion of these characteristics causes a poor control of the release rate.

Calcium phosphate granules, in particular hydroxyapatite granules, are used in liquid phase chromatography, because of their unique adsorption selectivity for biological molecules. They enable separation and purification in aqueous solution of biopolymers, proteins, enzymes, mono- and oligosaccharides to cite only a few (U.S. Pat. No. 5,217,699; U.S. Pat. No. 5,158,756; Re 35,340). Chromatographic granules should show the following characteristics: spherical shape and narrow size distribution, so as to allow uniform and compact filling of chromatographic columns; good mechanical resistance to wear and compression; diameters in the 50-300 micrometer range, in order to allow fast flow of mobile phases and minimize fouling, in particular in HPLC (high performance liquid chromatography). Moreover, chromatographic granules should show a finely divided and uniform porosity (open and closed porosity), in order to maximize adsorption capacity and selectivity.

Granulated calcium phosphate powders never show simultaneously all the characteristics requested for the various application fields presented above. Firstly, granules available in the range 50-1,000 micrometer are usually made by mere milling followed by size classification of sintered ceramic blocks shaped by dry-pressing or slip-casting. The so obtained granules, even though they might show controlled porosity, have irregular, often angular shapes which might elicit inflammatory reactions if they are used in medical applications (bone filling . . . ). For the same reason, such irregular granules are not adequate for use as carriers for controlled drug release, or as chromatographic stationary phase. The abovementioned process cannot produce granules with the narrow size distribution requested for achieving a good control of their resorption rate in biological conditions, or to prepare injectable cement pastes with good flowability. To achieve adequate granule characteristics, time-consuming and expensive complementary classification and polishing operations have to by applied.

Another way to make calcium phosphate granules in the abovementioned size range is to agglomerate fine calcium phosphate powders in the presence of water and/or organic binders. The binder can be put in contact with the powder in a fluidized bed (U.S. Pat. No. 5,034,352); alternatively it can be sprayed in a rotating thumble in which the dry powder is rolled (U.S. Pat. No. 5,702,677). The so obtained granules show usually a nice spherical shape and a good surface finish; however, they exhibit a very broad size distribution, and are difficult to make with a reasonably high compacity.

Other granulation techniques are well known in the field of ceramic powders, such as spray-drying of aqueous suspensions of fine powders which enable to produce granules in the size range 10-100 micrometers. One drawback of spray-drying is that hollow granules are often obtained, especially for larger sizes, with a broad granulometric distribution. Moreover, granules with sizes large than 100 micrometer can only be produced in extremely tall drying towers.

Thus, state-of-the-art calcium phosphate granules and their production processes show many severe drawbacks. In particular, current granulation techniques lack flexibility, and therefore cannot produce granules showing perfectly and independently controlled characteristics in terms of shape, size distribution and porosity.

DESCRIPTION OF THE INVENTION

Figure 1:
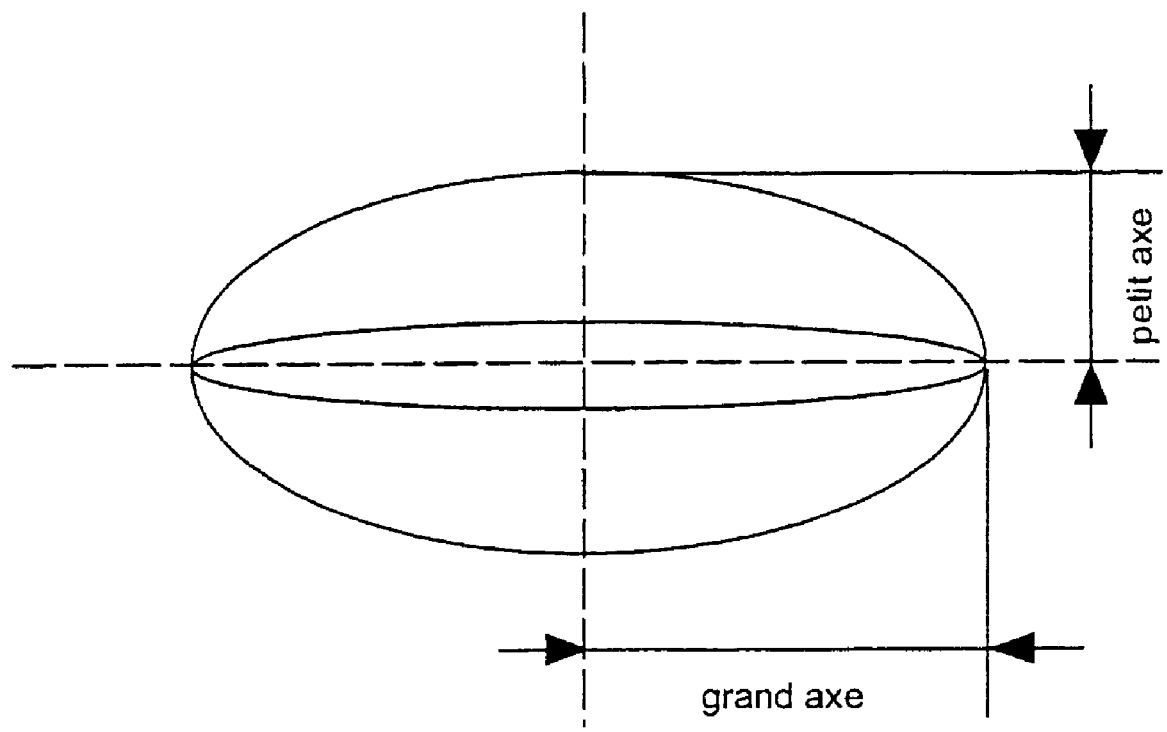
FIG. 1 depicts the major axis and the minor axis of a revolution ellipsoid.

The present invention aims in particular at solving the problems cited above. It relates to calcium phosphate microgranules in which the Ca/P atomic ratio is comprised between 1 and 2, and characterised by the fact that each microgranule exhibits substantially the shape of a revolution ellipsoid with major axis a and minor axis b and that the standard deviation relative to its average length of any of the two axes a or b is less than 5%.

The present invention relates also to a process enabling the production of calcium phosphate granules according to the specifications mentioned above. The present invention enables to make at will microgranules with independently controlled characteristics of shape, median size, size distribution and porosity.

Besides their very narrow size distribution, preferably centered around a median size comprised between 50 and 3,000 micrometers, the microgranules according to the present invention show an evenly distributed, optionally interconnected internal porosity, representing a volume fraction comprised between 0 and 70% of their apparent volume.

The granulation process according to the present invention operates with suspensions of calcium phosphate powders and/or other sparingly soluble calcium salts, to which various organic and/or inorganic additives may be added (deflocculants, plasticizers, binders, porogenic materials). Said suspensions may also contain at least one gelling agent. Special care is given to the preparation of said suspensions, in order to achieve the rheological behavior needed by the granulation process, during which a laminar jet of said suspensions is submitted to a physical perturbation leading to their fractionation into uniform droplets. The so obtained droplets are then pre-consolidated, for example by chemical reaction upon contacting them with some adequate aqueous solution of electrolyte, and subsequently washed and dried. In the case of ceramic microgranules, the final consolidation step can be effected by sintering at temperatures preferably comprised between 900 and 1,600° C.; alternatively, consolidation can be performed by chemical hardening in a water-saturated atmosphere at temperatures preferably comprised between 0 and 250° C. in the case of microgranules made of calcium phosphate cements.

As the case may be, microgranules according to the present invention consist of either thermally consolidated (sintered) ceramic materials, or chemically consolidated cementitious materials. For example, ceramic microgranules can consist of either hydroxyapatite, or β-tricalcium phosphate, or a mixture thereof. Cementitious microgranules can be obtained from a mixture in aqueous suspension of two powdered co-reactants, one having a relative acidic character, the other a relative basic character, which can dissolve simultaneously in water and elicit the subsequent precipitation of a less soluble compound. Various known calcium phosphate cementitious formulations can be used in the frame of the present invention. Especially well adapted to granulation according to the present invention is a new apatitic cement formulation consolidated by steaming at 121° C. in a water-saturated atmosphere, which consists of a mixture of monetite (anhydrous dicalcium phosphate) and calcium carbonate (calcite, aragonite, vaterite or mixtures thereof).

Microgranules according to the present invention consist in more or less flattened revolution ellipsoids, in particular spheres, with a very precise definition of their shape factor (±5% relative), the latter being comprised between 1 and 3. According to the present invention, the term "shape factor" means the ratio of the major axis over the minor axis of a revolution ellipsoid (see FIG. 1). According to this definition, a shape factor equal to 1 corresponds to a perfect sphere. With a shape factor equal to 1, the granulometric distribution can be extremely narrow, with a standard deviation less than 2% of the median diameter, the latter being comprised between 50 and 3,000 micrometers, preferably between 100 and 2,000 micrometers. The porous structure of the microgranules, corresponding to the volumetric fraction occupied by the pores, the average pore diameter and the degree of pore interconnection, can be controlled at will. Thus, the internal porosity of the microgranules is evenly distributed and can or not be interconnected according to the choice of the manufacturer. The porosity is controllable at will in the sense that the pore volume fraction can be varied between 0 and 70% of the total apparent volume, the pore size can be varied between 0.5 and 100 micrometers, preferably between 1 and 10 micrometers, the same with the size of the interconnexions between pores in the case of interconnected porosity. The desired porous structure can be achieved by playing with such parameters as, for instance, the solid/liquid ratio of the granulation suspension, the granulometry and concentration of a porogenic phase added to said suspension, and also the conditions of the final consolidation treatment (chemical hardening or sintering).

Special care must be paid to the preparation of the calcium phosphate powder(s) suspensions, in order to achieve the rheological properties needed by the granulation process. As the case may be, optimal suspension homogeneity and adequate rheological properties can be obtained by adding well selected hydrosoluble polymers, preferably biocompatible ones in the case of cementitious microgranules (e.g. polyacrylic acid). Adequate treatments are used for milling and deagglomerating the powders, in order to obtain well dispersed homogeneous suspensions.

The present invention also relates to a production process of calcium phosphate microgranules working with suspensions of at least one calcium phosphate powder and/or optionally other sparingly soluble calcium phosphate salts, to which optional organic or inorganic additives can be added (deflocculants, plasticizers, binders, porogenic agents), together with various types of gelling agents. The process according to the present invention consists in flowing a granulation suspension through a nozzle with a specified diameter, the emerging jet of suspension being converted into uniform droplets by submitting it to a physical perturbation. The so formed droplets are pre-consolidated by a chemical reaction taking place upon contacting them with some adequate electrolyte solution. According to the present invention, "electrolyte solution" means a solution containing solvated ions which can react with the gelling agent contained in the granulation suspension, thereby forming a sparingly soluble compound. Various combinations of gelling agent/gelling ions can be considered in the frame of the present invention, as for example: alginate and $Ca^{2+}$ or $Mg^{2+}$ ions; poly(vinylic acid) and borate ions or ammonia, . . . etc. In contrast to the state-of-the-art granulation processes, the granulation suspension according to the present invention is not atomised in the usual acception of this word: instead, it comes out of the granulation nozzle in the form of a laminar jet which, under the action of a physical perturbation, is fragmented into small uniform droplets. According to the present invention, the perturbation can be induced by mechanical, electromagnetical, pneumatic or piezoelectric vibration, or alternatively by electroacoustical irradiation; said perturbation can be applied to the nozzle and/or to the feeding appliance of the suspension, and/or to the reservoir containing the suspension. Moreover, it is very important to maintain a constant perturbation frequency, preferably in the range comprised between 50 and 20,000 Hz, in order to ensure a constant segmentation of the suspension jet, and hence uniformity of the generated droplets. The so formed droplets then fall down a column of adequate height, and take a more or less spherical shape under the action of surface tension. Eventually, they fall in an electrolyte solution where they are chemically pre-consolidated. According to the present invention, a slow torque is generated within the electrolyte solution, so as to adjust the residence time of the droplets and thereby their degree of pre-consolidation; by removing the falling droplets from the impact point, this torque also enables to avoid collisions between successive droplets, thus preventing their deformation.

Various set-ups can be used for minimizing deformation of the droplets upon impacting the surface of the electrolyte solution. For example, the droplets can be slacked by falling through a foam layer formed at the surface of the electrolyte solution, which thickness is comprised between 5 and 100 millimeters, preferably between 5 and 50 millimeters. On the other hand, adding selected surfactants or organic solvents such as, for instance, ethanol, propanol and the like, enables to reduce the surface tension of the electrolyte solution. In a preferred set-up of the present invention, the foam layer lying at the surface of the electrolyte solution is obtained with the use of organic surfactants and/or organic solvents.

According to the present invention, the viscosity of the granulation calcium phosphate suspension must be lower than 200 mPa·s; the diameter of the granulation nozzle is comprised between 50 and 3,000 micrometers.

The microgranules according to the present invention and their production process show several advantages. In particular, the characteristics of the microgranules produced according to the present invention (composition, shape, median diameter, particle size distribution and porosity) can be accurately controlled separately.

Calcium phosphate granules according to the present invention can be used in several applications in the biomedical field, thanks to their biocompatibility and their accurately controllable characteristics. According to the present invention, said granules can be made of calcium phosphate which Ca/P atomic ratio is comprised between 1 and 2. They consist of, either ceramic materials consolidated by thermal sintering, or cementitious materials consolidated chemically. Microgranules according to the present invention are characterized by: 1) a shape consisting in a flattened revolution ellipsoid, for instance a sphere, showing a shape factor comprised between 1 and 3 with a standard deviation less than 5%; 2) a very narrow granulometric distribution which, in the case of spherical granules, show a standard deviation smaller than 2% of their median diameter, the latter being comprised between 50 and 3,000 micrometers, preferably between 100 and 2,000 micrometers. Microgranules according to the present invention show a uniformly distributed porosity, which may or may not be interconnected; said porosity can be accurately controlled, in the sense that its volume fraction can be varied between 0 and 70% of the total apparent volume of the granules, the pore size can be controlled between 0.5 to 100 micrometers, preferably between 1 and 10 micrometers, the same control being applicable to the pore interconnection size. Finally, in the case of microgranules made of cementitious calcium phosphates, the chemical consolidation process confers to said granules a superior bioreactive character compared to materials sintered at high temperatures. Thus, cementitious microgranules according to the present invention keep a significant porosity which promote their fast bioresorption and enable their impregnation by pharmaceutically active substances.

Thus, microgranules made according to the present invention can be mixed to aqueous solutions containing polymers such as cellulose derivatives, to blood, or to injectable bone cements based on PMMA or self-setting calcium phosphate mixtures, and used for bone filling, bone augmentation or sealing of internal orthopedic prostheses. Alternatively, microgranules according to the present invention can be used for plasma-spray coating of metallic implants, as carriers for in vitro culture of bone cells, or as excipients for controlled release of pharmaceutical substances. Finally, microgranules according to the present invention can be used as immobile phase in liquid chromatography.

Illustrative examples of the present invention are presented below.

EXAMPLE 1

Ceramic Microgranules Made of β-Tricalcium Phosphate

An aqueous granulation suspension incorporating powdered β-tricalcium phosphate (β-TCP), poly(acrylic acid) (PAA) and sodium alginate (Na-alginate) is prepared for the production of ceramic β-TCP microgranules. The pH of said suspension is adjusted between 8 and 9 by addition of ammonia. Each liter of said suspension contains:

1,152 g of β-TCP powder
3.13 g of PAA
24.2 g of Na-alginate
593 g of demineralized water.

Figure 2:
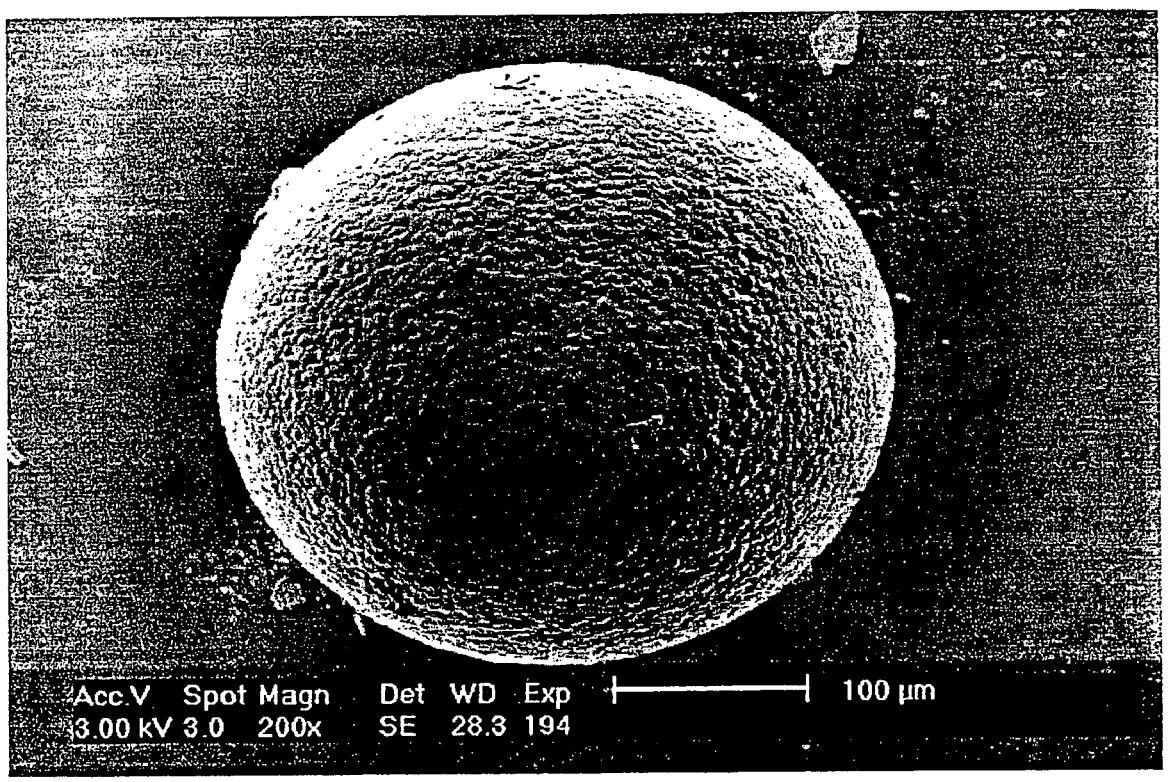
FIG. 2 is a photograph of a consolidated microbead.

Said suspension is flowed through a 200 micrometer diameter nozzle vibrated at a frequency comprised between 2,000 and 3,000 Hz. The formed droplets take their spherical shape while falling through a column. Said droplets are collected in an 2% weight $CaCl_2$ aqueous solution at ambient temperature, and pre-consolidated for 20 min in said solution in the form of microbeads. Said microbeads are then washed in plain water and subsequently dried in a rotating evaporator operated at 60° C. Said dried microbeads show a median diameter of 400 micrometers, with a standard deviation of 1-2% of the median diameter. The next step consists in a densification treatment of said microbeads by sintering them at 1,230° C. for 10 hours in a muffle furnace. After said sintering treatment, the consolidated microbeads show a median diameter of 300 micrometers, with a standard deviation of 1-2% of the median diameter (see FIG. 2). Their apparent density is 3.00 g/cm$^3$, which amounts 98% of the theoretical density of β-TCP and corresponds to a residual pore volume fraction lower than 2%.

EXAMPLE 2

Ceramic Microgranules Made of Hydroxyapatite

An aqueous granulation suspension incorporating powdered hydroxyapatite (HAp), poly(acrylic acid) (PAA) and sodium alginate (Na-alginate) is prepared for the production of ceramic hydroxyapatite microgranules. The pH of said suspension is adjusted between 8 and 9 by addition of ammonia. Each liter of said suspension contains:
  1,087 g of HAp powder
  4.04 g of PAA
  5.23 g of Na-alginate
  644 g of demineralized water.

Said suspension is flowed through a 350 micrometer diameter nozzle vibrated at a frequency comprised between 1,000 and 1,500 Hz. As for Example 1, the formed droplets are collected in an 2% weight CaCl$_2$ aqueous solution at ambient temperature, and pre-consolidated for 30 min in said solution in the form of microbeads. Said microbeads are then washed in plain water and subsequently dried in a rotating evaporator operated at 60° C. Said dried microbeads show a median diameter of 700 micrometers, with a standard deviation of 1-2% of the median diameter. The next step consists in a densification treatment of said microbeads by sintering them at 1,270° C. for 10 hours in a muffle furnace. After said sintering treatment, the consolidated microbeads show a median diameter of 600 micrometers, with a standard deviation of 1-2% of the median diameter. Their apparent density is 3.07 g/cm$^3$, which amounts about 97-98% of the theoretical density of HAp and corresponds to a residual pore volume fraction lower than 3%.

EXAMPLE 3

Microgranules Made of Hydroxyapatite Cement

An aqueous granulation suspension incorporating a stoichiometric mixture of powdered anhydrous dicalcium phosphate (DCP) and calcite (CC), poly(acrylic acid) (PAA) and sodium alginate (Na-alginate) is prepared for the production of hydroxyapatite cement microgranules. The pH of said suspension is adjusted between 8 and 9 by addition of ammonia. Each liter of said suspension contains:
  532.9 g of DCP powder
  261.3 g of CC powder
  130.1 g of HAp powder
  13.4 g of PAA
  5.50 g of Na-alginate
  6461.8 g of demineralized water.

Said suspension is flowed through a 150 micrometer diameter nozzle vibrated at a frequency comprised between 2,000 and 3,000 Hz. As for Examples 1 and 2, the formed droplets are collected in an 2% weight CaCl$_2$ aqueous solution at ambient temperature, and pre-consolidated for 30 min in said solution in the form of microbeads. Said microbeads are then washed in plain water and subsequently dried in a rotating evaporator operated at 60° C. Said dried microbeads show a median diameter of 400 micrometers, with a standard deviation of 1-2% of the median diameter. The next step consists in a densification treatment of said microbeads by steaming them at 121° C. for 1 hours in an autoclave. Said steaming treatment leads to the formation of HAp and release of water and carbon dioxide according to the following chemical reaction:

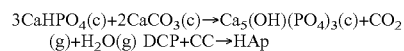

$$3CaHPO_4(c)+2CaCO_3(c) \rightarrow Ca_5(OH)(PO_4)_3(c)+CO_2(g)+H_2O(g) \; DCP+CC \rightarrow HAp$$

After said steaming treatment, the consolidated microbeads keep their median diameter of 400 micrometers, with a standard deviation of 1-2% of the median diameter. Their apparent density is 1.75 g/cm$^3$, which amounts about 55-56% of the theoretical density of HAp and corresponds to a pore volume fraction of 44-45%.

The invention claimed is:

1. Microgranules obtained by the following steps:
   a) preparing a suspension loaded with a calcium phosphate powder, and containing optionally at least one other sparingly calcium salt,
   b) optionally adding at least one inorganic or organic additive,
   c) optionally adding at least one gelling agent,
   d) converting the suspension into droplets by applying a perturbation, wherein a constant perturbation frequency is maintained and is in the range of between 50 and 20,000 Hz, and wherein an expulsion of the suspension through a granulation nozzle occurs in the form of a laminar jet that is fragmented into uniform droplets under the action of physical perturbation in the nature of mechanical, electromechanical, pneumatic or piezoelectric vibration or electroacoustical irradiation,
   e) consolidating the droplets, and
wherein each microgranule thus formed has roughly the shape of a revolution ellipsoid with a major axis a and a minor axis b, and having a microgranules granulometric distribution being such that its standard deviation relative to the average length of either of axes a or b is less than 5%.

2. Calcium phosphate microgranules obtained by performing the following steps:
   a) preparing a suspension loaded with calcium phosphate powder and containing optionally at least one other poorly soluble calcium salt,
   b) optionally adding at least one inorganic or organic additive,
   c) optionally adding at least one gelling agent,
   d) passing of the suspension through a nozzle,
   e) flowing out of the nozzle in the form of a laminar jet,
   f) perturbation of the laminar jet so that it is segmented into small droplets, wherein a constant perturbation frequency is maintained and is in the range of between 50 and 20,000 Hz, and wherein an expulsion of the suspension through the nozzle occurs in the form of the laminar jet that is fragmented into uniform droplets under the action of physical perturbation in the nature of mechanical, electromechanical, pneumatic or piezoelectric vibration or electroacoustical irradiation
   g) consolidating the droplets, and
wherein each microgranule thus formed having roughly the shape of a revolution ellipsoid with a major axis a and a minor axis b, and having a microgranules granulometric distribution being such that its standard deviation relative to the average length of either of axes a or b is less than 5%.

3. Microgranules according to claim 2, wherein the ratio of axis a over axis b varies between 1 and 3.

4. Microgranules according to claim 3, wherein both axes have the same length so that the ratio between axes a and b equals 1.

5. Microgranules according to claim 4, wherein the standard deviation relative to the average length of the axes is less than 2%.

6. Microgranules according to claim 2, wherein they show a uniformly distributed porosity representing a volumetric fraction comprised between 0 and 70% of their total apparent volume.

7. A process of producing calcium phosphate microgranules comprising the following steps:
  a) preparing a suspension loaded with a calcium phosphate powder, and containing optionally at least one other sparingly calcium salt,
  b) optionally adding at least one inorganic or organic additive,
  c) optionally adding at least one gelling agent,
  d) converting the suspension into droplets by applying a perturbation, wherein a constant perturbation frequency is maintained and is in the range of between 50 and 20,000 Hz, and wherein an expulsion of the suspension through a granulation nozzle occurs in the form of a laminar jet that is fragmented into uniform droplets under the action of physical perturbation in the nature of mechanical, electromechanical, pneumatic or piezoelectric vibration or electroacoustical irradiation,
  e) consolidating the droplets, and
wherein each microgranule thus formed having roughly the shape of a revolution ellipsoid with a major axis a and a minor axis b, and having a microgranules granulometric distribution being such that its standard deviation relative to the average length of either of axes a or b is less than 5%.

8. A process of producing calcium phosphate microgranules comprising the following steps:
  a) preparing a suspension loaded with calcium phosphate powder and containing optionally at least one other poorly soluble calcium salt,
  b) optionally adding at least one inorganic or organic additive,
  c) optionally adding at least one gelling agent,
  d) passing of the suspension through a nozzle,
  e) flowing out of the nozzle in the form of a laminar jet,
  f) perturbation of the laminar jet so that it is segmented into droplets, wherein a constant perturbation frequency is maintained and is in the range of between 50 and 20,000 Hz, and wherein an expulsion of the suspension through the nozzle occurs in the form of the laminar jet that is fragmented into uniform droplets under the action of physical perturbation in the nature of mechanical, electromechanical, pneumatic or piezoelectric vibration or electroacoustical irradiation and
  g) consolidating the droplets.

9. A process according to claim 8, wherein passing of the suspension through a nozzle comprises using a nozzle having a diameter between 50 and 3,000 micrometers.

* * * * *